US011254935B2

(12) United States Patent
Eveleth et al.

(10) Patent No.: US 11,254,935 B2
(45) Date of Patent: Feb. 22, 2022

(54) METHODS AND COMPOSITIONS FOR USE OF NON-CODING RNA IN CELL CULTURING AND SELECTION

(71) Applicants: HocusLocus, LLC, Albany, NY (US); Universität für Bodenkultur, Vienna (AT)

(72) Inventors: Edward Eveleth, Albany, NY (US); Nicole Borth, Vienna (AT); Scott A. Tenenbaum, Selkirk, NY (US); Francis J. Doyle, II, Delanson, NY (US); Zachary Edward Wurz, Amsterdam, NY (US)

(73) Assignees: HocusLocus, LLC, Albany, NY (US); Universität fur Bodenkulture, Vienna (AT)

( * ) Notice: Subject to any disclaimer, the term of this patent is extended or adjusted under 35 U.S.C. 154(b) by 28 days.

(21) Appl. No.: 15/515,834

(22) PCT Filed: Oct. 3, 2015

(86) PCT No.: PCT/US2015/053897
§ 371 (c)(1),
(2) Date: Mar. 30, 2017

(87) PCT Pub. No.: WO2016/054616
PCT Pub. Date: Apr. 7, 2016

(65) Prior Publication Data
US 2017/0298350 A1 Oct. 19, 2017

Related U.S. Application Data

(60) Provisional application No. 62/059,573, filed on Oct. 3, 2014.

(51) Int. Cl.
*C12N 15/11* (2006.01)
*C12N 5/10* (2006.01)
*C12N 15/85* (2006.01)

(52) U.S. Cl.
CPC .............. *C12N 15/111* (2013.01); *C12N 5/10* (2013.01); *C12N 15/85* (2013.01); *C12N 2310/141* (2013.01); *C12N 2320/10* (2013.01); *C12N 2330/51* (2013.01); *C12N 2800/24* (2013.01); *C12N 2840/102* (2013.01); *C12N 2840/105* (2013.01); *C12N 2999/007* (2013.01)

(58) Field of Classification Search
CPC .. C12N 15/111; C12N 5/10; C12N 2310/141; C12N 2840/102; C12N 2840/105
USPC ........................................................ 435/325
See application file for complete search history.

(56) References Cited

U.S. PATENT DOCUMENTS

| 8,841,438 B2 | 9/2014 | Tenenbaum et al. |
| 9,719,085 B2 | 8/2017 | Tenenbaum et al. |
| 2005/0215497 A1 | 9/2005 | Harel-Bellan et al. |
| 2008/0120733 A1 | 5/2008 | Hafner et al. |
| 2011/0311985 A1 | 12/2011 | Hahn |

FOREIGN PATENT DOCUMENTS

| WO | 2010091837 A1 | 8/2010 |
| WO | WO-2013/182553 A2 | 12/2013 |

OTHER PUBLICATIONS

Barron (2011, Journal of Biotechnology, 151:204-211).*
Miyoshi (2010, Mol Genet Genomics, 284:95-103).*
Supplemental European Search Report for EP15847837.0 dated Apr. 26, 2018, 8 pages.
Lin, et al., Intronic MicroRNA (miRNA), Journal of Biomedicine and Biotechnology, vol. 2006, Article ID 26818, Jan. 2006, pp. 1-13.
Doyle et al. (2014) "Trans-Regulation of RNA-Binding Protein Motifs by MicroRNA," Frontiers in Genetics 5(79):1-10.
Huang et al. (2009) "Advances in research on intronic miRNAs feedback regulation of their host genes," Bull Acad Mil Med Sci 33(6):580-582, 595.
Miyoshi et al. (2010) "Many ways to generate microRNA-like small RNAs: non-canonical pathways for microRNA production," Molecular Genetics and Genomics 284(2):95-103.
Riley et al. (2012) "EBV and human microRNAs co-target oncogenic and apoptotic viral and human genes during latency," The EMBO Journal 23:2207-2221.
Theimer et al. (2013) "Characterization of trans-acting RNA-based switches for gene expression control," International Conference of RNA Nanotechnology and Therapeutics pp. 25.

* cited by examiner

*Primary Examiner* — Valarie E Bertoglio
(74) *Attorney, Agent, or Firm* — Goodwin Procter LLP (57) ABSTRACT

Described herein are methods and compositions for producing a gene of interest (GOI) which, in certain embodiments, can reduce the metabolic burden on cells and reduce decoupling of GOI production from marker production, as compared to prior art methods. The methods relate to positive selection and negative selection approaches to establishing high GOI-producing cell lines, e.g., CHO lines. In certain embodiments, the methods comprise transfecting a cell with (a) an oligonucleotide comprising a GOI and a non-coding RNA, and (b) an oligonucleotide encoding a selection protein; wherein the non-coding RNA promotes or inhibits production of the selection protein. The cell producing the GOI can be identified and/or selected as a result of or by detecting the absence or the presence of the selection protein.

19 Claims, 5 Drawing Sheets

METHODS AND COMPOSITIONS FOR USE OF NON-CODING RNA IN CELL CULTURING AND SELECTION

CROSS REFERENCE TO RELATED APPLICATIONS

This application is a national stage entry under 35 U.S.C. 371 of international patent application number PCT/US15/53897 filed Oct. 3, 2015 which claims the benefit of U.S. Provisional Application 62/059,573 filed on Oct. 3, 2014. The entire contents of these applications are incorporated herein by reference in their entirety.

BACKGROUND OF THE INVENTION

Billions of dollars' worth of biological products, such as antibodies, vaccines and proteins, are produced from Chinese Hamster Ovary (CHO) cells each year. Even small improvements in the yield in CHO cells can have a large economic impact. Process development has focused on achieving the maximum amount of active product, the Gene of Interest (GOI). Optimization of production to achieve higher recombinant protein yields of the GOI can be achieved in two primary ways. The first approach is to increase the cell density (i.e., cells per volume) of the process. This may be accomplished through process development (e.g., batch, fed-batch, perfusion, etc.) and improvements to growth medium. By increasing the cells per volume per day, higher levels of product are produced. During the last 20 years, the increases in product titers for antibodies from around 0.1-0.3 g/l to today's 2-10 g/l were mostly achieved by improvements in processes and media, while the specific productivity of a single cell did not increase to a similar degree. Further increases in cell densities are limited due to the inherent size limitations, so future productivity improvements will need to come from improvements in the selection of cells with extremely high and efficient productivity, q, (i.e., the amount of GOI produced per cell).

This second approach strives to increase the specific productivity through cell line development. Cell line development may include both sub-cloning the cell line to select higher producing clones and the use of gene amplification. Drug resistance has been the tool of choice in the biopharmaceutical industry to induce gene amplification by combining the GOI with a selectable gene to accomplish increased production levels. Two gene amplification systems commonly used in CHO cells are the dihydrofolate reductase (DHFR) system using methotrexate (MTX) resistance, and the glutamine synthetase (GS) system using methionine sulfoxamine (MSX) resistance. Gene amplification is accomplished by transforming cells with recombinant DNA consisting of the GOI along with the gene for DHFR, for example, and then cultivating them at increasingly higher levels of MTX. The DHFR enzyme catalyzes the conversion of folate to tetrahydrofolate, while MTX inhibits the production of tetrahydrofolate which deprives cells of nucleoside precursors (hypoxanthine and thymidine) and eventually kills them. CHO cells with increased copies of the DHFR gene, and therefore higher levels of tetrahydrofolate, are thus selected. Using productivity-per-cell approaches, scientists have increased expression levels more than 1,000-fold from the initially very low levels.

Figure 1:
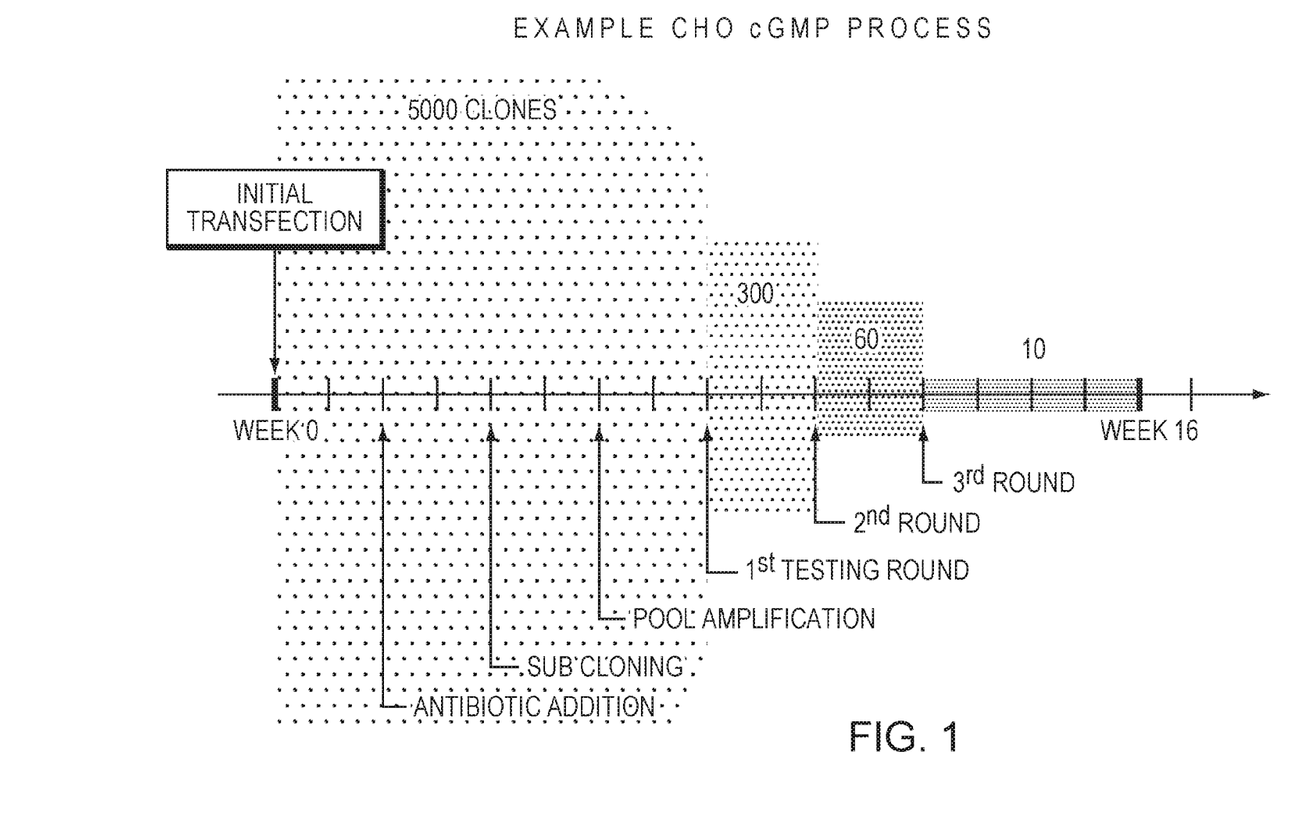

The cell line development process itself, exemplified in FIG. 1, is burdened by (1) the lengthy time involved, currently cell line development in large companies with set platform techniques is 4-9 months, and (2) the workload, which generally involves initial testing of approximately 5,000 clones. Most cGMP processes start out working in a pool after transfection. There is a two week delay for recovery after addition of antibiotic followed by a pool amplification step (concurrent with increased concentration of MTX or MSX). Another 2-3 weeks is required for recovery, followed by subcloning of good pools (2 weeks) and initial testing of 2,000-5,000 candidates. From those candidates about 300 lines are selected and placed into small shaker tubes (5-10 ml) for the next round of testing which follows two weeks later. Typically, 60 or more candidates are selected for the next stage, and each must be individually grown and analyzed from discrete 125 ml shaker flasks over a 2 week process. Those 60 are then assessed for product quality attributes, and 10 are selected for stability testing and small bioprocess testing in 2-6 liter containers. Four weeks are required for expansion and bioprocess runs, with stability testing to continue for 4 months potentially in increasingly large containers. Selection is conducted initially only by productivity, and later, on a larger scale, the more important product quality is assessed.

CHO process development has focused on maximizing the amount of active product, referred to as the Gene of Interest (GOI), while ensuring the best possible quality. The use of a drug resistance gene as a selectable proxy is the current standard for selection of successfully transformed CHO cells, which are then sub-cloned and screened for production of the GOI. This basic approach has not changed substantially in over 20 years, but has two major drawbacks. First, the current methods require production of the additional antibiotic resistant gene which can compete with the GOI for limited cellular resources, placing additional metabolic drain on the cells. Second, although frequently introduced within the same vector, expression of the antibiotic resistance or selection gene is a proxy and not directly coupled to the GOI, which can create a misleading expectation of final GOI production rate and can result in the costly maintenance of non-productive cells. In fact, current positive section techniques are only 50%-90% efficient because the production of the selectable marker is not coupled directly to the production of the GOI. (See, Fan, L., et al. (2012) BIOTECHNOLBIOENG 109(4): 1007-15 and Kim, Y. G., et al. (2012) BMC Biotechnol 12:24.) During the amplification process, for example, when gene copy number is increased through DNA replication errors, the selective pressure is on the amplification of the selective marker gene, while the GOI is only secondarily amplified due to its close proximity to the selection marker. Thus, cells that amplify the selective marker gene without the GOI actually have a selective advantage because they produce only one foreign gene.

Current transcriptional based approaches, i.e. expressing different genes or using alternative DNA vectors, cannot ameliorate these issues. Accordingly, improvements are needed to improve yield of GOI from CHO and other cells. In particular, methods that (1) reduce metabolic burden and/or (2) tie selection directly to GOI transcription, and therefore to production of the GOI, are needed to improve GOI yield.

SUMMARY OF THE INVENTION

Described herein are methods and compositions for producing a gene of interest (GOI), which, in certain embodiments, can reduce the metabolic burden on cells and reduce decoupling of GOI production from marker production, as compared to prior art methods. The methods relate to positive selection and negative selection approaches to establishing high GOI-producing cell lines, e.g., CHO lines. In certain embodiments, the methods comprise transfecting a cell with (a) an oligonucleotide comprising a GOI and a non-coding RNA, and (b) an oligonucleotide encoding a selection protein; wherein the non-coding RNA promotes or inhibits production of the selection protein. The cell producing the GOI can be identified and/or selected as a result of or by detecting the absence or the presence of the selection protein.

Metabolic burden on cells is reduced because the marker for GOI-expressing cells used in the selection process is a non-coding RNA and not, e.g., a protein with antibiotic resistance that competes for translation with the GOI. Even in a positive selection approach, the selection process can be carried out using an artificially transcribed mRNA or a DNA molecule that is not maintained by the cell long-term. This means that during the production phase of harvesting the GOI, the cell must only produce the GOI itself (or two GOI in the case of, e.g., antibodies), rather than a GOI and a marker protein.

A further advantage of certain embodiments described herein is the reduction in decoupling of GOI production from marker production, as compared to prior art methods. Closely coupling the non-coding RNA and the GOI (e.g., in an intron or untranslated region (UTR)) makes it less likely that the non-coding RNA, and thus the selection protein, will be expressed in the absence of expression of the GOI, compared to prior art methods. Accordingly, there will be few selected cells that do not produce the GOI, leading to an increased efficiency in expression of the GOI.

The methods described herein allow for negative selection of GOI-producing cells. In one example, the selection protein is a gene that is lethal to the cell, and the non-coding RNA prevents production of the lethal gene. Because production of the GOI and the non-coding RNA are coupled, a cell will survive only if the non-coding RNA (and thus the GOI) is produced. In certain embodiments of a negative selection method, the non-coding RNA is an siRNA, which harnesses the cell's innate siRNA pathway to turn off the expression of a pro-apoptotic gene encoded on an artificially transcribed mRNA, which had been introduced into the cell. When the GOI is produced, the siRNA inhibits production of the pro-apoptotic protein, allowing the cell to survive.

A positive selection approach can be used as an alternative to, or in addition to, a negative selection approach. In a positive selection approach, a non-coding RNA, such as an miRNA, stabilizes an sxRNA to turn on the expression of an oligonucleotide comprising a selection protein, e.g., an antibiotic resistance gene or a fluorescent marker. Cells expressing the marker can then be selected, e.g., by addition of an antibiotic or by fluorescence-activated cell sorting (FACS).

In one aspect, described herein is a method for identifying a cell producing a gene of interest (GOI), the method comprising transfecting the cell with (a) an oligonucleotide comprising the GOI and one or more non-coding RNA, and (b) an oligonucleotide encoding a selection protein; wherein the one or more non-coding RNA promotes or inhibits production of the selection protein. The method further comprises identifying the cell producing the GOI by detecting the absence or the presence of the selection protein.

In certain embodiments, the one or more non-coding RNA is one non-coding RNA. In other embodiments, the one or more non-coding RNA is a plurality of non-coding RNAs. The plurality of non-coding RNAs can be a plurality of copies of the same non-coding RNA, or the non-coding RNAs can be different.

In certain embodiments, the one or more non-coding RNA promotes cell survival and/or the amount of GOI produced per cell. In certain embodiments, the non-coding RNA is ebv-miR-BART10-3p or mirR-7.

In certain embodiments, the oligonucleotide encoding a selection protein further comprises an sxRNA capable of being stabilized by the one or more non-coding RNA, thereby promoting translation of the selection protein.

In certain embodiments, the method further comprises transfecting the cell with a second selection protein, wherein the second selection protein is a death gene and wherein the one or more non-coding RNA inhibits production of the death gene.

In certain embodiments, the non-coding RNA is an miRNA or siRNA. In certain embodiments the one or more non-coding RNA is one or more miRNA or one or more siRNA capable of binding to and inhibiting the oligonucleotide encoding a selection protein.

In certain embodiments, the cell is a Chinese Hamster Ovary (CHO) cell or a human embryonic kidney (HEK) cell.

In certain embodiments, the selection protein is an antibiotic resistance gene, a fluorescent marker, a cell surface marker, or a cell death gene.

In certain embodiments, the one or more non-coding RNA is encoded in an intron. In certain embodiments, the one or more non-coding RNA is an intron. In certain embodiments, the one or more non-coding RNA is in a UTR.

In certain embodiments, the method further comprises transfecting the cell with a second GOI and a second non-coding RNA. In certain embodiments, the first and second non-coding RNAs are the same.

In certain embodiments, the first and second non-coding RNAs are different. The oligonucleotide encoding the selection protein further encodes a second selection protein or the method can comprise transfecting the cell with a second oligonucleotide encoding a second selection protein. In this embodiment, the second non-coding RNA promotes or inhibits translation of the second selection protein.

In certain embodiments, the second non-coding RNA is encoded in an intron. In certain embodiments, the second non-coding RNA is an intron. In certain embodiments, the one or more non-coding RNA is in a UTR.

In another aspect, the method relates to promoting survival of cells producing a gene of interest (GOI). The method comprises transfecting cells with (a) an oligonucleotide comprising the GOI and one or more siRNA, and (b) an oligonucleotide encoding a protein lethal to the cells; wherein the one or more siRNA, when transcribed with the gene of interest, is capable of inhibiting production of the lethal protein, thereby promoting survival of the cells producing the GOI.

In certain embodiments, the one or more siRNA is one siRNA. In other embodiments, the one or more siRNA is a plurality of siRNAs. The plurality of siRNAs can be a plurality of copies of the same siRNA, or a plurality of copies of different siRNAs.

In certain embodiments, the one or more siRNA promotes cell survival and/or the amount of GOI produced per cell. In certain embodiments, the one or more siRNA is ebv-miR-BART10-3p or mirR-7. In certain embodiments, the cell is a Chinese Hamster Ovary (CHO) cell or a human embryonic kidney (HEK) cell. In certain embodiments, the one or more siRNA is encoded in an intron. In certain embodiments, the one or more siRNA is an intron.

In yet another aspect, disclosed herein is a transgenic cell comprising: (a) an oligonucleotide comprising a gene of interest (GOI) and one or more non-coding RNA, and (b) an oligonucleotide encoding a selection protein; wherein the one or more non-coding RNA promotes or inhibits translation of the selection protein.

In certain embodiments, the oligonucleotide encoding a selection protein further comprises an sxRNA capable of being stabilized by the one or more non-coding RNA, thereby promoting or inhibiting translation of the selection protein.

In certain embodiments, the non-coding RNA is capable of stabilizing the sxRNA, thereby promoting association of the sxRNA with an RNA-binding protein (RBP). In certain embodiments, the one or more non-coding RNA is an siRNA capable of binding to and inhibiting the oligonucleotide encoding a selection protein.

In certain embodiments, the cell is a Chinese Hamster Ovary (CHO) cell or a human embryonic kidney (HEK) cell.

In certain embodiments, the one or more non-coding RNA is one or more miRNA or one or more siRNA.

In certain embodiments, the one or more non-coding RNA promotes cell survival and/or the amount of GOI produced per cell. In certain embodiments, the one or more non-coding RNA is ebv-miR-BART10-3p or mirR-7.

In certain embodiments, the selection protein is an antibiotic resistance gene, a fluorescent marker, a cell surface marker, or a cell death gene.

In certain embodiments, the one or more non-coding RNA is encoded in an intron. In certain embodiments, the one or more non-coding RNA is an intron. In certain embodiments, the one or more non-coding RNA is in a UTR.

In certain embodiments, the cell further comprises a second GOI and a second non-coding RNA. In certain embodiments, the second non-coding RNA is encoded in an intron. In certain embodiments, the second non-coding RNA is an intron. The second non-coding RNA can be one or more second non-coding RNA.

In certain embodiments, the first and second non-coding RNAs are the same.

In certain embodiments, the first and second non-coding RNAs are different and the oligonucleotide encoding the selection protein further encodes a second selection protein, or the cell comprises a second oligonucleotide encoding a second selection protein, wherein the second non-coding RNA promotes or inhibits translation of the second selection protein.

In another aspect, an oligonucleotide comprising a gene of interest (GOI) and a non-coding RNA is disclosed herein, wherein, when expressed in a cell with an oligonucleotide encoding a selection protein, the non-coding RNA is capable of promoting or inhibiting translation of the selection protein.

In certain embodiments, the cell is a Chinese Hamster Ovary (CHO) cell or a human embryonic kidney (HEK) cell.

In certain embodiments, the non-coding RNA is an miRNA or an siRNA.

In certain embodiments, the non-coding RNA promotes cell survival and/or the amount of GOI produced per cell. In certain embodiments, the non-coding RNA is ebv-miR-BART10-3p or mirR-7.

In certain embodiments, the selection protein is an antibiotic resistance gene, a fluorescent marker, a cell surface marker, or a cell death gene.

In certain embodiments, the non-coding RNA is encoded in an intron. In certain embodiments, the non-coding RNA is an intron. In certain embodiments, the one or more non-coding RNA is in a UTR.

BRIEF DESCRIPTION OF THE DRAWINGS

FIG. 1 depicts an exemplary prior art CHO cGMP process. The process starts with 5,000 clones and is reduced to 10 high producing clones over a 16 week period. The process can take longer depending upon the selection platforms used.

FIG. 3 shows another schematic diagram of certain embodiments of the negative and positive selection methods described herein. In step 1, a plasmid comprising the GOI and encoding a non-coding RNA is transfected into a cell. In step 2, once the non-coding RNA has been expressed, an oligonucleotide encoding a selection protein is transfected into the cell. In cells expressing the GOI, the non-coding RNA will either promote or inhibit production of the selection protein. In step 3, for a positive selection, the non-coding RNA stabilizes a stem loop to promote production of a selection protein gene via binding of an RBP. For a negative selection, the non-coding RNA inhibits production of a gene that is lethal to the cell, such that only cells producing the GOI will survive.

DETAILED DESCRIPTION

1. Introduction

Described herein are methods and compositions which relate to combining the regulation of gene expression by a non-coding RNA (e.g., an miRNA or an siRNA) with a selection protein to allow for selection of high GOI producing CHO cells. A primary advantage of our approach is that the non-coding RNA serving as the surrogate for GOI production is closely coupled to the GOI (e.g., co-expressed from an intron transcribed from within the GOI), ensuring the emergence of so-called escape mutants is minimized. Positive and/or negative selection can then be performed by co-transfecting the oligonucleotide comprising the non-coding RNA and GOI with a second oligonucleotide encoding an mRNA comprising sxRNA switch or siRNA regions. The co-expressed miRNA acts as a trigger for either positive or negative mRNA-sxRNA-siRNA selection approaches.

In the case of sxRNA mediation, positive selection entails the use of the engineered HSL structure sensitive to the non-coding RNA (e.g., miRNA) trigger to turn ON production of a selection protein transgene such as an antibiotic resistance protein, a fluorescent protein for FACS or a cell surface protein for magnetic cell-sorting. The counterpart, negative selection, is typified by the well documented siRNA response, and will instead use the non-coding trigger in an siRNA capacity to turn OFF expression of an apoptosis gene or other death gene resulting in the death of cells not robustly producing the GOI. Cell selection can be optimized by using positive and negative sxRNA/siRNA technologies alone or in combination, in series over time or in parallel at the same time, and repeated using different techniques at different time intervals.

There are several major benefits to this overall approach. First, by replacing the continuous expression of DHFR or GS with the positive and negative selection approached described herein, we significantly reduce the metabolic stress on the cells from the need to produce an additional protein, resulting in increased production of the GOI. Specifically, in a negative selection approach, no selection protein is produced in cells producing GOI. Even in a positive selection approach, the selection protein can be introduced on an artificially transcribed mRNA or on a DNA molecule that is not maintained by the cell long-term. Thus, the cell must only devote metabolic resources to the selection protein during a short selection phase, leaving more cellular machinery free to express the GOI during the production cycle.

Second, in certain embodiments, coupling the production of our trigger miRNA directly to the real-time production of the GOI mRNA has additional benefits. The efficiency of any selection methods can be increased by reducing the error rate caused by disjointed production of the marker and GOI. Additionally, the methods described herein are advantageous because they avoid the stress placed on high producing GOI cells by the addition of the antibiotics and elimination of the time needed for recovery after the addition of antibiotics.

Using the methods described herein, GOI production can be further increased by use of a non-coding RNA or RNAs that can increase q (the amount of GOI produced per cell). Several studies have shown that incorporating an miRNA into CHO cells can lead to increased production. The chosen miRNA can have varied functions including reducing apoptosis.

The methods and compositions described herein are particularly advantageous for biomanufacturing, but can also be used for any purpose that requires protein production, e.g., basic research.

2. Methods

These two selection techniques, positive and negative, available because of the co-transcribed miRNA, can be used alone or in combination to maximize gene amplification. They can also be used repeatedly in any order or combination. mRNA employing either strategy can be transfected as one round of selection, or a mixture of mRNA employing both strategies can be transfected simultaneously for a single round of selection. In certain embodiments, continuous transfection techniques are used, which allow the mRNA to be included in the media. In certain embodiments, negative selection is preferred at the start of the process and positive selection is preferred in later stages.

a. Positive sxRNA Selection

Our positive sxRNA-mRNA selection approach allows the selection of optimal GOI producing cells using the non-coding RNA to turn "ON" expression of a marker protein. In a positive selection approach, a non-coding RNA, such as an miRNA, stabilizes an sxRNA downstream of a selection protein, e.g., an antibiotic resistance gene, or a fluorescent marker. Cells expressing the marker can then be selected, e.g., by addition of an antibiotic or by fluorescence-activated cell sorting (FACS).

b. Negative siRNA Selection

For negative selection, the non-coding RNA can be an siRNA which reduces the expression of a selection protein, rather than increasing it as with positive selection and sxRNA. In certain embodiments, a non-coding RNA (e.g., an siRNA) suppresses expression of a pro-apoptotic death gene, such as diphtheria toxin A, ΔNBax, Bid, Caspase 9, Bad, or Bim. An oligonucleotide (e.g., mRNA) encoding a selection protein can be designed to include a sequence that is a BART10 sensitive siRNA degradation target. In cells co-expressing a GOI and BART10 siRNA, BART10 siRNA will degrade the pro-apoptotic mRNA while the cells without will express the pro-apoptotic gene and die, resulting in an active selection of miRNA carrying cells.

An mRNA encoding a selection protein can be rendered sensitive to virtually any siRNA-mediated cleavage by inserting cognate siRNA target sites (i.e., complementary sequences to the trigger miRNA) either 5' or 3' of the ORF. Multiple siRNA target sites can be added to increase efficiency.

An alternative negative selection method comprises use of an sxRNA to ablate a stem-loop sequence, as described in more detail below.

c. Transfection Methods

Methods for transfecting oligonucleotides, including DNA and RNA, are well known in the art and may be suitable for use in the methods described herein. An oligonucleotide, e.g., a DNA plasmid comprising a GOI and non-coding RNA (or a selection protein, with or without an sxRNA) can be transfected into a cell using any number of methods currently known in the art. Exemplary methods include calcium phosphate precipitation, calcium chloride precipitation, electroporation, polyethyleneimine, lipofection or any lipid based vesicle technique, Adenovirus, Adeno-associated Virus, and lentiviral and retroviral transduction.

Methods for transfecting RNA into a cell are well known in the art and may be suitable for use in the methods described herein, including, for example, for transfecting cells with RNA, e.g., an mRNA encoding a selection protein and optionally, a sxRNA. Exemplary methods include nucleofection using either a NEON electroporator (Invitrogen) or a Nucleofector®II device (Lonza, Md.). Both DNA and mRNA transfection can be performed using NEON which achieves 95% transfection efficiency with high viability (greater than 90%). Transfection using any method that allows mRNA to reach cytoplasm is also possible.

3. Cells

The compositions disclosed herein relate to a transgenic cell comprising: (a) an oligonucleotide comprising a gene of interest (GOI) and a non-coding RNA, and (b) an oligonucleotide encoding a selection protein; wherein the non-coding RNA promotes or inhibits translation of the selection protein. In certain embodiments, the selection protein is a death gene and the non-coding RNA is an siRNA that is capable of inhibiting production of the death gene. In certain embodiments, in addition to inhibiting production of the death gene, the non-coding RNA independently promotes cell survival and/or the amount of GOI produced per cell. In certain embodiments, the non-coding RNA is ebv-miR-BART10-3p ("BART10") or mirR-7. In certain embodiments, the non-coding RNA is in an intron. In certain embodiments, the non-coding RNA is a UTR.

In certain embodiments, the oligonucleotide encoding a selection protein further comprises an sxRNA capable of being stabilized by the non-coding RNA (e.g., a miRNA), thereby promoting or inhibiting translation of the selection protein. The non-coding RNA is capable of stabilizing the sxRNA, thereby promoting association of the sxRNA with an RBP. In certain embodiments, the non-coding RNA is an siRNA capable of binding to and inhibiting the oligonucleotide encoding a selection protein.

In certain embodiments, the cell further comprises a second GOI and a second non-coding RNA. The first and second non-coding RNAs can be the same or different. When different, the oligonucleotide encoding the selection protein further encodes a second selection protein, or the cell comprises a separate, second oligonucleotide encoding a second selection protein, wherein the second non-coding RNA promotes or inhibits translation of the second selection protein. In certain embodiments, the second non-coding RNA is encoded in or is an intron. In certain embodiments, the second non-coding RNA is encoded in a UTR.

Cells appropriate for use as a starting strain for the methods and compositions described herein, are known in the art, and include, e.g., Chinese Hamster Ovary (CHO) cells, human embryonic kidney (HEK) cells, baby hamster kidney (BHK) cells, human fibrosarcoma cells, PER.C6® cells (Crucell/Janssen Pharmaceuticals, Inc.), EB66® cells (Vivalis), NSO, the baculovirus cell lines Sf9, Sf-21, TN368, and BTI-TN-5B1-4, and any metazoan derived cell line utilizing the HSL motif for post-transcriptional regulation.

4. Gene of Interest (GOI)

Any GOI that can be expressed in CHO cells or other cells described herein can be used in connection with the methods and compositions described herein. Exemplary GOIs include α-glucosidase, Laronidase, Ig-CTLA4 fusion, N-acetylgalactosamine-4-sulfatase, luteinizing hormone, Factor VIII (Advate), α-galactosidase, interferon-β, Factor VIII, tissue plasminogen activator (Tenecteplase, Activase), TNFα receptor fusion (Enbrel), Factor IX, follicle stimulating hormone, β-glucocerebrosidase, deoxynuclease I, and erythropoietin (Epogen/Procrit, Aranesp).

In certain embodiments, two GOI are produced in the same cell. For example, for antibody production, both the light and heavy chain genes can express the same non-coding RNA, or each can express a different non-coding RNA. If there are two different non-coding RNAs, selection can be performed first directed against one miRNA, and then directed against the other miRNA. Either positive or negative selection can be performed on either miRNA in any order. If two of the same non-coding RNAs are used, either positive or negative selection can be tuned to respond to only extreme levels of expression of the miRNA trigger (i.e., expression levels indicative of both GOI being expressed). Exemplary antibodies (Abs) include, e.g., monoclonal Abs such as anti-EGFR mAb, anti-VEGF mAb, anti-IgE mAb, anti-CD11a mAb, anti-TNFα mAb, anti-CD52 mAb, anti-HER2 mAb, anti-PD1 mAb, anti-PD-1 mAb, and anti-CD20 mAb.

5. Non-coding RNA

In certain embodiments of the invention, the non-coding RNA is an RNA interference sequence (e.g., an miRNA, an shRNA, an siRNA, a piRNA, an snoRNA, an lncRNA, or dsRNA nucleotide sequence) that can stabilize a sxRNA or inhibit (e.g., silence) a selection protein. RNAi sequences for use in the agents of the invention may be either commercially available (e.g., Dharmacon, Ambion) or the practitioner may use one of several publicly available software tools for the construction of viable RNAi sequences.

Non-coding RNAs can be any exogenously supplied RNA that promotes or inhibits production of a selection protein. For positive selection, a non-coding RNA binds to the flank regions of an sxRNA, stabilizing the structure of the sxRNA to promote interaction with an RBP or other translation-promoting protein. For negative selection, a non-coding RNA inhibits a selection protein, e.g., by binding to and causing degradation of the mRNA encoding the selection protein. Alternatively, the non-coding RNA can bind to an sxRNA and disrupt base pairing of the secondary structure (e.g., a stem-loop) of the sxRNA, thereby preventing expression of a nearby encoded selection protein.

A non-coding RNA can be, but is not limited to, a viral polynucleotide, a bacterial polynucleotide, an polynucleotide expressed in a neoplastic cell, or a polynucleotide characteristic of a protein deficiency. Non-coding RNA can be found in, for example, but not limited to, a virally- or bacterially-infected cell, a neoplastic cell, a diseased cell, a tissue, a cell culture, or a sample containing polynucleotides (e.g., a blood sample).

For positive selection, the sequence of the non-coding RNA also should allow for the sxRNA to base pair with a favorable energy minimization to promote preferential binding, i.e., the non-coding RNA should bind preferentially to the sxRNA as compared to a natural target. For example, the calculated MFE (minimum free energy) structure should be such that the non-coding RNA is predicted to hybridize the sxRNA's flank regions as desired (rather than the non-coding RNA binding to a natural target, or the sxRNA folding with itself and the non-coding RNA folding with itself or the sxRNA and the non-coding RNA hybridizing in a manner other than what is desired).

As described herein, a non-coding RNA is encoded on an oligonucleotide with a GOI. In certain embodiments, the non-coding RNA and GOI are on the same oligonucleotide (e.g., plasmid vector), but have different promoters. In certain embodiments, the non-coding RNA and GOI are on the same transcript to physically couple expression of the GOI with expression of the non-coding RNA. In certain embodiments, a non-coding RNA is expressed in an intron or an untranslated region (UTR) of a GOI. In certain embodiments, the non-coding RNA is the intron (see, e.g., a "mirtron" in International Patent Publication No. WO2010029303) or the UTR. In certain embodiments, a plurality of non-coding RNA is in an intron or in a UTR. The plurality of non-coding RNAs can be the same or different. Expressing a non-coding RNA in an intron is well understood. Commercially available plasmids that co-express a miRNA and a reporter are commercially available (see, e.g., Cell Biolabs, Inc., San Diego, Calif.). Standard transcription factors and initiation sequences can be used to express the non-coding RNA. Any technique that closely couples expression of a GOI to expression of the non-coding RNA is sufficient.

In certain embodiments, a non-coding RNA, such as an miRNA, can provide some independent benefit to its overexpression in cells, such as reducing apoptosis, increasing q, reducing autophagy, increasing proliferation, and improving cell cycle, chaperoning, secretion, protein folding, and metabolic changes to improve production of the product of the gene of interes. For example, ebv-miR-BART10-3p has been shown to play a role in inhibiting apoptosis in human cells. Epstein Barr Virus (EBV) likely uses BART10 to dampen the cell's natural defense response and keep the cell intact until the virus is ready. Thus, BART10 can be used as a non-coding RNA as described herein, but in addition can independently promote cell viability by inhibiting apoptosis. As an alternative miRNA, for example, miR-7 was found to be down-regulated at low culture temperature, and its overexpression can significantly increase q in CHO cells at 37° C. Other mRNAs that can affect cell cycle include miR-21, miR-16 and let-7b. (Kim et al. (2012) APPL.MICROBIOL.BIO-TECHNOL 93:917-930.) Further exemplary non-coding RNAs that allow for higher productivity and/or secretion include miR-125a-3p, miR-149, miR-1271, miR-1275, miR-1285, miR-1287, miR-1293, miR-183, miR-185*, miR-193b*, miR-1978, miR-23b*, miR-299-3p, miR-557, miR-612, miR-644a, miR-885-3p, miR892a. (See WO2013/182553.)

a. siRNA

A short interfering RNA (siRNA) is a short (usually about 20-25 base pairs in length), double-stranded RNA molecule, which plays a number of roles, including interfering with expression of genes having sequence complementary to the siRNA. The mechanism of siRNA and the RISC complex degrading mRNA is well understood, and these principles can be used to design an siRNA for use as a non-coding RNA in the methods and compositions described herein. In one embodiment, an mRNA is designed to comprise siRNA sites, i.e., one or more nucleotide sequences that are perfectly complementary to the siRNA. In certain embodiments, use of an siRNA achieves a reduction in protein expression of 80%, i.e. 20% of the expected protein expression compared to expression levels without a silencing miRNA. Sequences perfectly complementary to the trigger miRNA in the 3' and 5' UTRs of the selection mRNA can be used with the methods and compositions described herein.

b. miRNA

A microRNA (miRNA) is a single-stranded RNA, usually between about 18-25 nucleotides in length, which, in a natural setting, binds to a complementary region of an mRNA and cleaves or otherwise represses translation of the mRNA. In accordance with the methods and compositions described herein, an miRNA can act to bind to and cleave or otherwise repress translation of a selection protein mRNA to facilitate negative selection. Alternatively, an miRNA can be used in a positive selection approach to bind to and stabilize an sxRNA switch as described in more detail below.

6. Selection Protein

Any selection protein, in one or two parts, employing any method to differentiate cells can be used for this process. For positive selection methods, any markers known in the art can be used. Selection protein include antibiotic resistance genes, fluorescent markers, and cell surface markers. Antibiotic resistance genes and related systems can function as a selection proteins, e.g., expressing DHFR and selecting for MTX resistance, expressing GS and selecting for MSX resistance, expressing the Pac gene, which encodes a puromycin N-acetyl-transferase (PAC), and selecting for puromycin resistance.

Fluorescent markers such as mCherry or green fluorescent protein (GFP) can be used, with selection performed using fluorescence-activated cell sorting (FACS). Cell surface markers can be used, such as the membrane protein CD4, which can be stained easily by addition of a fluorescent antibody for FACS sorting or a magnetic antibody for selection using magnetic cell sorting.

For negative selection methods, the following exemplary selection systems, known in the art, can be used. Pro-drug systems, such as Herpes Simplex Virus Thymidine Kinase/Ganciclovir (HSV-TK/GCV) or Cytosine Deaminase/5-Fluorocytosine (CD/5-FU), can be used in which a combination of an expressed protein and small molecule cause cell death. The pro-drug/activator method can be advantageous for negative selection because it can be refined at the level of pro-drug administration; namely, if activator expression is low, more pro-drug could be used, or if activator expression is high, less pro-drug is required.

An apoptosis gene, such as Caspase-9 (C9) or any member of the Caspase family, caspase activators, or larger CARD superfamily of proteins, which play a central role in triggering and executing apoptosis, can be used. Additional suitable selection proteins include, but are not limited to, pro-apoptotic members of the BCL-2 and BAG domain and family of proteins, such as Bax, Bad, Bid, Bim. BIRC proteins, CARD, DEATH, and TRAF domain containing proteins. Other proteins suitable for use as a selection protein are those which artificially trigger pathways normally resolved for external stimuli, such as TRAIL or other members of the TNF ligand superfamily, which act as a ligand for TNF and other death receptors. Other suitable proteins are those affecting the oxidative and DNA damage response pathways, which can halt cell cycle, but also trigger apoptosis under certain circumstances, which are activated by lynchpin pathway proteins such as TP53, CHK2, but also many others. Most pro-apoptotic proteins are inactive until an inhibitory region is removed, and the expression of active sub-regions of these proteins is also viable, such as ANBax. Pathogen-derived pro-apoptotic proteins like diphtheria toxin fragment A can also be used.

7. sxRNA

In certain embodiments described herein, a trans-RNA switching mechanism called structurally interacting RNA or "sxRNA" is used, which relies on the expression of a miRNA to turn "on" and "off" the expression of an ectopic gene of choice. See U.S. Pat. No. 8,841,438, issued Sep. 23, 2014, incorporated by referenced herein in its entirety.

Figure 2:
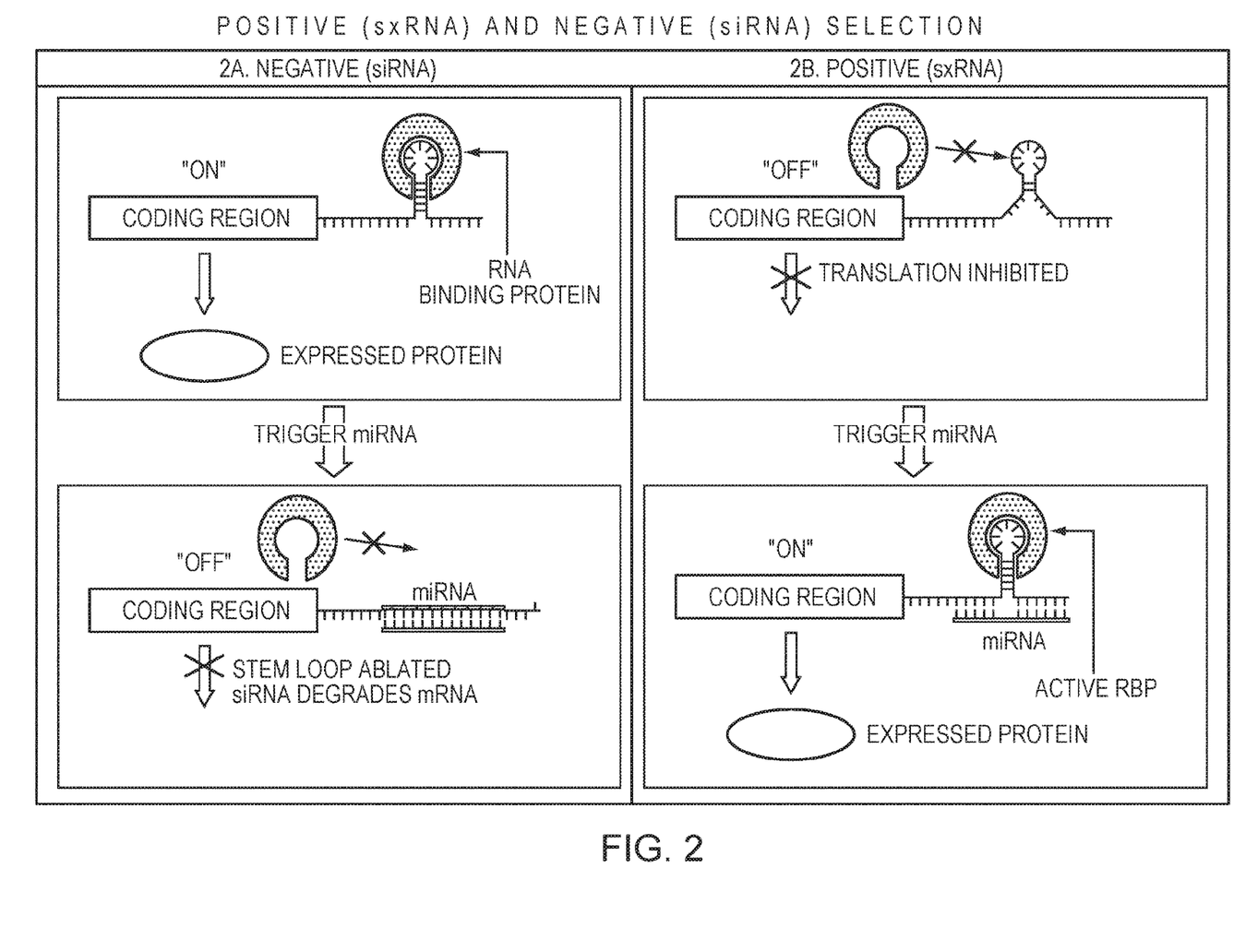
FIG. 2 shows a schematic diagram of certain embodiments of the negative and positive selection methods described herein. 2A shows an exemplary negative selection method in which the non-coding RNA is an miRNA that ablates an RBP binding site (a stem loop) downstream of the coding region for a selection protein preventing its expression. 2B shows an exemplary positive selection method in which the non-coding RNA is an miRNA that stabilizes a stem loop, promoting formation of an RBP binding site. Binding of the RBP to the stem loop promotes expression of the selection protein encoded upstream.

As shown in FIG. 2, sxRNA technology involves the use of a miRNA to "switch" the structure of an ectopically delivered mRNA to alter its ability to bind a cellular regulatory RBP. Most RBPs regulate gene expression by interacting with specific structural binding sites, often stem-loop structures, formed within the untranslated region (UTR) of the mRNA. Certain RNA binding proteins (RBPs), when bound to mRNA, increase translation by several orders of magnitude. A "switch" can be placed within an oligonucleotide encoding a selection protein (e.g., an mRNA encoding a selection protein) such that a trans-interaction with a non-coding RNA (e.g., an miRNA) can ablate or stabilize an RBP binding site. Use of the sxRNA switch according to the methods described herein allows for selection of cells with high CHO cell productivity without the need for the continuous expression of an antibiotic resistance protein.

In certain embodiments, the sxRNA is designed based on a histone stem loop (HSL), which recruits the histone stem loop binding protein (SLBP). The presence or absence of an HSL in the 3' UTR of an mRNA can result in a 10-25 fold difference in the level of expression of histone messages depending upon the ability of the HSL to attract SLBP. Most histone messages have no poly-A tail, and require the HSL and SLBP to translate efficiently.

sxRNA switches can be designed to function in positive selection or negative selection. In one embodiment, a positive sxRNA switch is designed by modifying a stable HSL motif to weaken its structural potential so that the histone SLBP is unable to or less likely to bind to the sxRNA. The flank region at the base of the stem-loop is engineered to be complimentary to the trigger non-coding so that the stem loop is re-formed when the non-coding RNA interacts with the sxRNA-mRNA. This restores function of the motif and allows binding of the SLBP, inducing active translation of an upstream selection protein. In another embodiment, switches for negative selection are designed by making an HSL, or portions of it, complementary to the non-coding RNA (e.g., a miRNA). The interaction of the two sequences will disrupt the HSL (e.g., by ablating the stem loop) and prevent SLBP binding.

sxRNA switches for positive selection have been designed using endogenous miRNA to turn on translation of a selection protein sxRNA-mRNA using triggers non-coding RNA such as hsa-miR-122, a liver specific miRNA highly expressed in Huh7 cells, hsa-miR-302, an induced pluripotent cell (iPSC) specific miRNA, and ebv-miR-BART10-3p, an miRNA produced by the Epstein-Barr virus. The ARGO and RISC complex do not appear to inhibit these sxRNA interactions. Accordingly, use of an sxRNA switch allows one to control expression of any GOI when an appropriate non-coding RNA (e.g., miRNA) trigger is used.

Any RNA containing secondary structure that recruits an RBP can be used as an sxRNA. For example, RNA sequences that recruit IREBP, EIF4e, EIF4g or polyA binding protein can be used. For example, an IRE in the 3' UTR will attract IREBP and increase expression, while an IRE in the 5' UTR will attract IREBP and decrease expression. Natural or modified nucleotides can be used to increase survival and durability of the mRNA.

EXAMPLES

Example 1

Negative Selection

Figure 3:
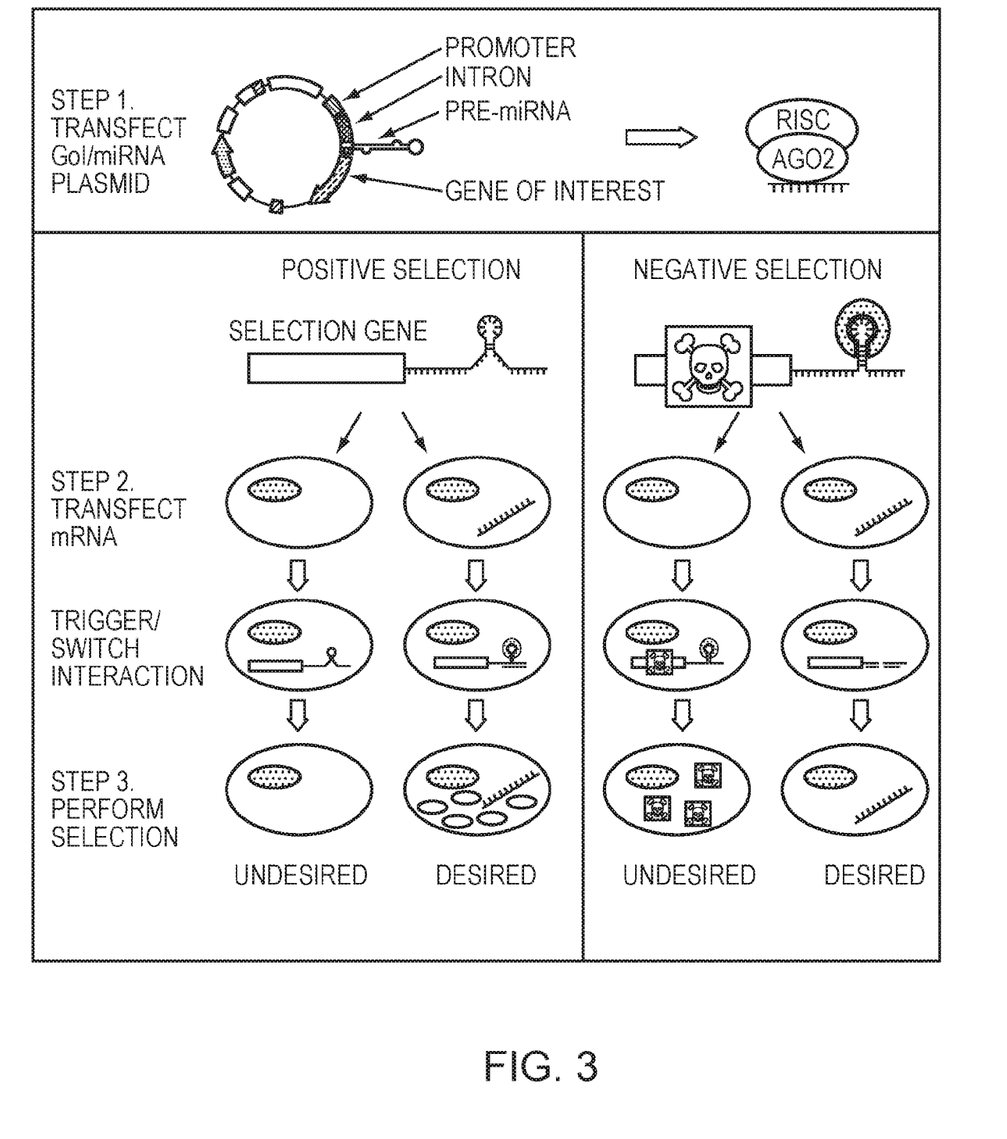

For a negative selection, an miRNA co-expressed with a GOI turns off expression of a transiently transfected mRNA that would otherwise be translated. When the transfected mRNA is a pro-apoptotic or other cell death effector gene, this can result in cells that are not expressing the miRNA to die while keeping the cells with the trigger miRNA and therefore GOI alive (FIG. 2A, FIG. 3).

In this experiment, a HEK293 cell line was created that stably expresses the BART10 miRNA from an intron in GFP, which was used as an easily measurable surrogate GOI (GFP/BART10+ cells). Cells were classified as stable after 30 days of passaging with no loss or dilution of the GFP signal. BART10 production was verified using qRT-PCR for the miRNA compared to the wild type HEK293s. Plasmids were designed with the ΔNBax pro-apoptotic protein downstream of a T7 promoter and either one or three copies of a duplex of BART10 siRNA target sites (2 or 6 sites total) in the 3' UTR of ΔNBax. The target sites themselves are fully complementary to the predicted BART10 siRNA sequence. The plasmids were used as templates for in vitro transcription and the resulting mRNA was used to challenge GFP/BART10+ HEK293s and their wild-type counterparts.

Initial data demonstrated results consistent with predictions. In cells which were carrying BART10 miRNA, the ΔNBax mRNA was rapidly degraded and the cells survived. However, the cells without BART10 expressed ΔNBax, resulting mitochondrial depolarization and apoptosis. To show that negative selection functions in a heterogeneous mix of cells, we mixed the wild type and GFP/BART10+ HEK293 cells in varying ratios and transfected them with the ANBax mRNA. As expected, the amount of cell death was inversely proportional to the overall BART10+ HEK293 content of the cell mixture—when more BART10+ cells comprised the mixed population, fewer cells died. Fluorescent microscopy indicated enrichment for GFP/BART10+, precisely the result one would expect from a successful selection of the GFP/BART10 cells.

Example 2

Positive Selection

Figure 4:
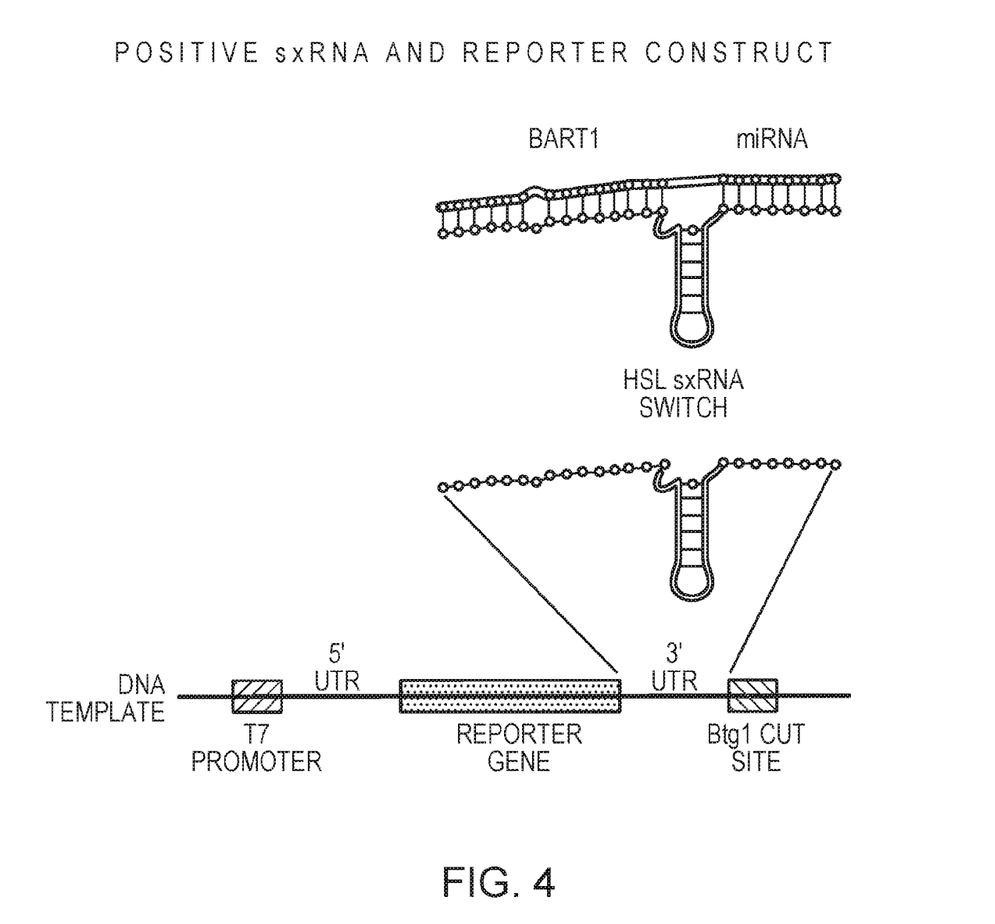
FIG. 4 shows the design of a second oligonucleotide comprising a fluorescent selection protein (reporter gene) and a downstream sxRNA. The stem loop of the sxRNA is stabilized by binding of a BART10 miRNA, which promotes expression of the fluorescent selection protein (reporter gene).
Figure 5:
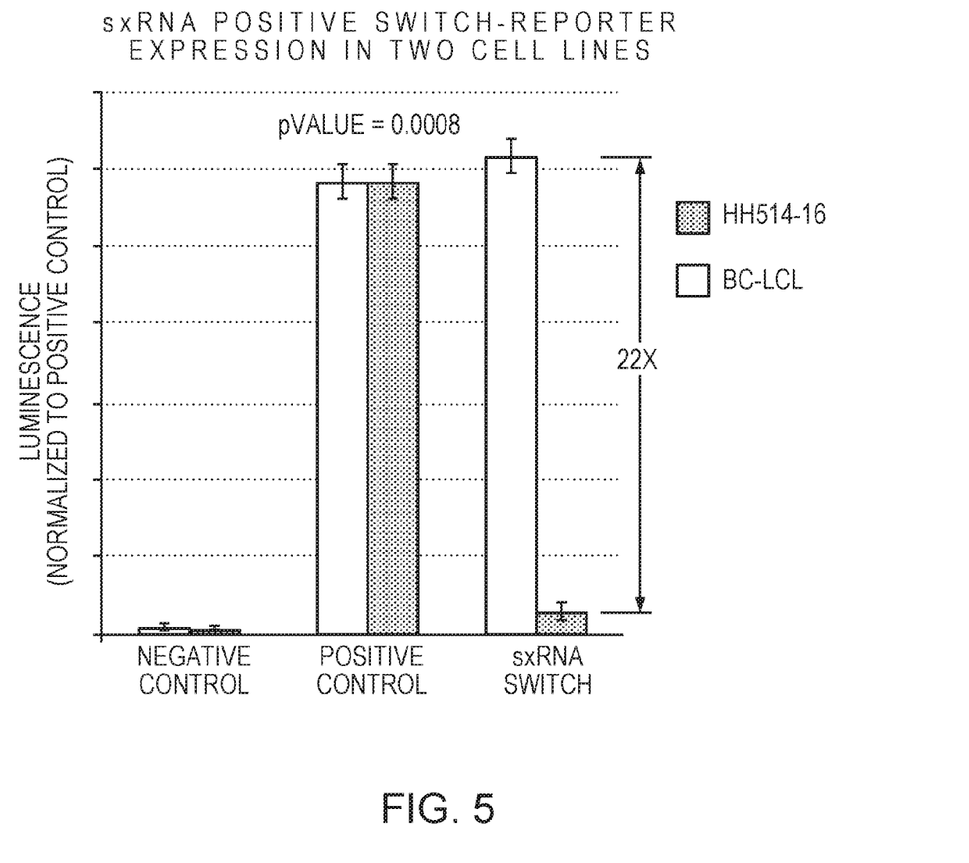
FIG. 5 shows a bar graph indicating luminescence measured from cells nucleofected the in vitro T7 transcribed mRNA shown in FIG. 4. One cell line was infected with an EBV strain expressing BART10 (HH514-16 cells), while the other cell line was infected with an EBV variant that lacked the BART10 gene (LCL cells). As shown, the BART10 miRNA promotes expression of the fluorescent dramatic, and statistically significant change in expression.

In an exemplary positive selection method, BART10 miRNA was used as a non-coding RNA. BART10 miRNA is not predicted to have cross-reactivity with the CHO genome. We designed an HSL-based switch that is predicted to interact with BART10 to form a 3-way junction and placed this sxRNA switch in the 3' UTR of a luciferase reporter mRNA as shown in FIG. 4. We then nucleofected the in vitro T7 transcribed mRNA into two cell lines (FIG. 5). One was infected with an EBV strain expressing BART10 (HH514-16 cells), while the other was infected with an EBV variant that lacked the BART10 gene (LCL cells). FIG. 5 depicts the resulting expression levels and shows a dramatic and statistically significant change in expression.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

The entire disclosure of each of the patent documents, scientific publications, and other database references disclosed hereinabove is expressly incorporated herein by reference for all purposes.

What is claimed is:

1. A method for identifying a cell producing a protein encoded by a gene of interest (GOI), the method comprising:
   (1) transfecting the cell with
      (a) a first oligonucleotide comprising the GOI and one or more non-coding RNA, and
      (b) a second oligonucleotide encoding a selection protein, wherein the one or more non-coding RNA promotes or inhibits production of the selection protein, wherein the second oligonucleotide encoding a selection protein further comprises an sxRNA;
         (i) wherein the sxRNA is stabilized by the one or more non-coding RNA to promote translation of the selection protein or (ii) wherein the sxRNA comprises secondary structure that is disrupted by the one or more non-coding RNA to inhibit translation of the selection protein; and
   (2) detecting the absence or the presence of the selection protein to identify the cell producing the protein encoded by the GOI.

2. The method of claim 1, wherein the one or more non-coding RNA promotes cell survival and/or the amount of protein encoded by the GOI produced per cell.

3. The method of claim 1, wherein the one or more non-coding RNA is ebv-miR-BART10-3p or mirR-7.

4. The method of claim 1, comprising transfecting the cell with a oligonucleotide encoding a second selection protein, wherein the second selection protein is a lethal protein and wherein the one or more non-coding RNA inhibits production of the lethal protein.

5. The method of claim 1, wherein the cell is a Chinese Hamster Ovary (CHO) cell or a human embryonic kidney (HEK) cell.

6. The method of claim 1, wherein the selection protein is an antibiotic resistance protein, a fluorescent marker, or a cell surface marker, or a lethal protein.

7. The method of claim 1, wherein the one or more non-coding RNA is encoded in an intron of the GOI.

8. The method of claim 1, further comprising transfecting the cell with a second GOI and a second non-coding RNA, wherein the second GOI and the second non-coding RNA are located on the same oligonucleotide.

9. The method of claim 8, wherein the second non-coding RNA is encoded in an intron of the second GOI.

10. The method of claim 8, wherein the first and second non-coding RNAs are the same.

11. The method of claim 8, wherein
   (1) the first and second non-coding RNAs are different and wherein
   (2) the oligonucleotide encoding the selection protein further encodes a second selection protein, or
   wherein the method comprises transfecting the cell with a second oligonucleotide encoding a second selection protein, wherein
   (2) the second non-coding RNA promotes or inhibits translation of the second selection protein.

12. A method for promoting survival of cells producing a protein encoded by a gene of interest (GOI), the method comprising:
   transfecting cells with (a) an oligonucleotide comprising the GOI and one or more siRNA, and (b) an oligonucleotide encoding a protein lethal to the cells;
   wherein the one or more siRNA inhibits production of the protein lethal to the cells to promote survival of the cells producing the protein encoded by the GOI.

13. A method for identifying a cell producing a protein encoded by a gene of interest (GOI), the method comprising:
   (1) transfecting one or more cells with
      (a) a first oligonucleotide comprising a gene of interest (GOI) and one or more non-coding RNA, and
      (b) a second oligonucleotide encoding a selection protein, wherein the one or more non-coding RNA is an miRNA or an siRNA that binds and inhibits translation of the second oligonucleotide encoding a selection protein; and
   (2) identifying or selecting the cell producing the protein encoded by the GOI by detecting the absence of the selection protein.

14. The method of claim 13, wherein the cell is a Chinese Hamster Ovary (CHO) cell or a human embryonic kidney (HEK) cell.

15. The method of claim 13, wherein the selection protein is a fluorescent marker, a cell surface marker, or a lethal protein.

16. The method of claim 13, wherein the one or more non-coding RNA is encoded in an intron of the GOI.

17. The method of claim 13, wherein the selection protein is a lethal protein.

18. The method of claim 13, further comprising: transfecting the cell with an oligonucleotide encoding a second selection protein, wherein the second selection protein is a lethal protein and wherein the one or more non-coding RNA inhibits expression of the lethal protein.

19. The method of claim 13, further comprising: transfecting the cell with a second GOI and a second non-coding RNA, wherein the second GOI and the second non-coding RNA are located on the same oligonucleotide.

* * * * *